(12) United States Patent
Zipfel et al.

(10) Patent No.: US 10,842,425 B2
(45) Date of Patent: Nov. 24, 2020

(54) METHOD FOR THE MASK-ETCHING OF A PIERCING ELEMENT

(71) Applicant: Roche Diabetes Care, Inc., Indianapolis, IN (US)

(72) Inventors: Marzellinus Zipfel, Freiburg (DE); Angel Lopez-Mras, Pforzheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 617 days.

(21) Appl. No.: 15/378,434

(22) Filed: Dec. 14, 2016

(65) Prior Publication Data

US 2017/0086726 A1  Mar. 30, 2017

Related U.S. Application Data

(60) Division of application No. 14/221,990, filed on Mar. 21, 2014, now Pat. No. 9,522,566, which is a
(Continued)

(30) Foreign Application Priority Data

Sep. 23, 2011 (EP) .................................... 11182455

(51) Int. Cl.
*A61B 5/00* (2006.01)
*A61B 5/15* (2006.01)
(Continued)

(52) U.S. Cl.
CPC ...... *A61B 5/150282* (2013.01); *A61B 5/1411* (2013.01); *A61B 5/157* (2013.01);
(Continued)

(58) Field of Classification Search
CPC ......... H01L 27/11582; H01L 27/11556; H01L 21/31116; A61M 37/0015;
(Continued)

(56) References Cited

U.S. PATENT DOCUMENTS 5,591,139 A * 1/1997 Lin .................... A61M 37/0015
604/264
6,334,856 B1 * 1/2002 Allen .................. A61B 5/14514
604/191
(Continued)

FOREIGN PATENT DOCUMENTS

| EP | 2 263 544 A1 | 12/2010 |
| EP | 2 272 429 A1 | 1/2011 |
| WO | WO 2006/066744 A1 | 6/2006 |

*Primary Examiner* — May A Abouelela
(74) *Attorney, Agent, or Firm* — Woodard, Emhardt, Henry, Reeves & Wagner, LLP

(57) ABSTRACT

A method is disclosed for the mask-etching of a piercing element having an elongate shaft, a distally protruding tip, a proximal holding part, and a laterally open collecting channel that collects bodily fluid and extends along the shaft as far as the area of the tip, wherein a side of a double-sided etching mask is applied respectively to the two sides of a substrate and, under the action of an etching agent, the piercing element is formed as a part made by chemical blanking, wherein a channel side of the etching mask is provided with a channel etching slit for unilateral etching of the collecting channel.

20 Claims, 4 Drawing Sheets

Related U.S. Application Data continuation of application No. PCT/EP2012/068426, filed on Sep. 19, 2012.

(51) Int. Cl.
    *B01D 67/00*     (2006.01)
    *A61B 5/157*     (2006.01)
    *B44C 1/22*     (2006.01)
    *C23F 1/02*     (2006.01)

(52) U.S. Cl.
    CPC .. *A61B 5/150022* (2013.01); *A61B 5/150358* (2013.01); *A61B 5/150419* (2013.01); *A61B 5/150519* (2013.01); *B01D 67/0034* (2013.01); *B01D 67/0058* (2013.01); *B44C 1/227* (2013.01); *C23F 1/02* (2013.01)

(58) Field of Classification Search
    CPC ......... A61M 2037/003; A61B 17/3403; A61B 2018/1425; A61F 2002/3082; A61F 2002/30838
    USPC ........... 600/537, 583; 606/181, 182; 216/11; 435/29
    See application file for complete search history.

(56) References Cited

U.S. PATENT DOCUMENTS

| | | | |
|---|---|---|---|
| 6,749,575 B2 * | 6/2004 | Matriano | A61B 10/0045 600/564 |
| 7,344,499 B1 * | 3/2008 | Prausnitz | A61M 37/0015 600/309 |
| 7,824,382 B2 * | 11/2010 | Reihl | A61B 5/14528 604/264 |
| 2002/0177788 A1 | 11/2002 | Hodges et al. | |
| 2002/0188221 A1 | 12/2002 | Sohrab | |
| 2004/0236271 A1 * | 11/2004 | Theeuwes | A61B 17/205 604/47 |
| 2004/0267205 A1 * | 12/2004 | Stemme | A61M 37/0015 604/173 |
| 2005/0232813 A1 | 10/2005 | Karmali | |
| 2006/0084942 A1 * | 4/2006 | Kim | A61K 9/0021 604/890.1 |
| 2006/0293611 A1 * | 12/2006 | Calasso | A61B 5/150419 600/583 |
| 2007/0197937 A1 * | 8/2007 | Sarofim | B01L 3/502707 600/583 |
| 2007/0299365 A1 * | 12/2007 | Calasso | A61B 5/14532 600/583 |
| 2008/0040919 A1 * | 2/2008 | Griss | A61M 37/00 29/777 |
| 2008/0249435 A1 | 10/2008 | Haar et al. | |
| 2012/0004614 A1 * | 1/2012 | Stumber | A01K 11/005 604/173 |
| 2012/0058506 A1 * | 3/2012 | Gao | A61B 5/1411 435/29 |
| 2012/0116437 A1 * | 5/2012 | Horauf | A61B 5/1411 606/181 |
| 2012/0172820 A1 * | 7/2012 | Cannehan | A61M 37/0015 604/272 |
| 2013/0184609 A1 * | 7/2013 | Lee | A61B 17/205 600/573 |

* cited by examiner

METHOD FOR THE MASK-ETCHING OF A PIERCING ELEMENT

This application is a divisional of U.S. patent application Ser. No. 14/221,990 filed Mar. 21, 2014, now U.S. Pat. No. 9,522,566, which is a continuation of international Application No. PCT/EP2012/068426 filed Sep. 19, 2012, which claims priority to European Patent Application No. 11182455.3, filed Sep. 23, 2011, which are hereby incorporated by reference.

An embodiment of the invention relates to a method for the mask-etching of a piercing element which has an elongate shaft, a distally protruding tip, a proximal holding part, and a laterally open collecting channel that collects bodily fluid and extends along the shaft as far as the area of the tip, in which method a side of a double-sided etching mask is applied respectively to the two sides of a substrate and, under the action of an etching agent, the piercing element is formed as a part made by chemical blanking, wherein a channel side of the etching mask is provided with a channel etching slit for unilateral etching of the collecting channel. An embodiment of the invention further relates to a correspondingly produced piercing element.

An etching method is disclosed in WO 2006/066744 A1 for producing disposable piercing elements for the recovery of small amounts of samples, such as those that are withdrawn in situ from a skin incision as capillary blood for blood glucose determinations. The latter document, however, proposes an etching mask layout for a capillary channel that is open at the front and closed at the proximal end, wherein the piercing tip protrudes distally from the rear face directed away from the channel. A problem also lies in avoiding interference contours in the piercing process caused by the channel walls jutting up at the front end.

Proceeding from this, the object of the invention is to further optimize the etching methods known in the prior art, and the piercing elements generated by said methods, and to improve the collecting of samples and the transfer of samples in integrated diagnostic systems.

This object is achieved by the combination of features indicated in the independent claims. Advantageous embodiments and developments of the invention are set forth in the dependent claims.

The invention is based on the concept of optimizing the end of the collecting channel for the collection and transfer of samples. It is thus proposed, according to an embodiment of the invention, that a proximal and/or distal end portion of the channel etching slit is designed to taper toward the end of the slit.

It is thus possible to ensure, on the one hand, that, during the etching process, the channel cross section in the front distal tip area tapers or at least remains constant and no bone-shaped widening occurs at the channel end as a result of flow processes of the etching agent. Even if such a "bone formation" were to be classed at first as non-critical for the uptake of liquid in the tip area, this could nevertheless lead to etching-through in the area of the tip, on account of the reduced material thickness. Accordingly, the collecting channel would not be able to be guided far forward, and the increased distance between tip and channel end would necessarily lead to a deeper depth of incision and, therefore, to an increased sensation of pain. In order to reduce the depth of incision and to ensure optimal collection of samples or blood, it is therefore essential that the capillary channel already comes into contact with blood or tissue fluid during the incision under the skin. Such a configuration of an etched part is achieved using an etching mask in which the channel etching slit is guided as far as the distal tip area and thereby tapers.

On the other hand, the tapering of the etching slit at the proximal end has the effect that the etched collecting channel terminates at the rear end with a constant or even decreasing capillary diameter, such that the capillary transport is not interrupted too early, as would be unavoidable in the case of capillary widening by standard etching techniques.

In an advantageous embodiment, the end portion of the channel etching slit is tapered linearly, such that the etched collecting channel extends in the direction of the taper with a constant or continuously decreasing cross-sectional area.

In order to support a capillary-active transfer of samples, it is advantageous if the channel etching slit is positioned in a proximal region of the etching mask, such that the etched collecting channel opens out at the front end on the holding part.

A further improvement in terms of sample handling in an integrated test configuration can be achieved by virtue of the fact that the etching mask is provided with a flange-forming area, which adjoins the channel etching slit in the proximal direction, and that, by undercutting the flange-forming area, a preferably straight flange edge forming the mouth of the collecting channel is generated, in particular for flanging a test element onto the holding part.

In order to give the mouth a planar limit, it is advantageous if the flange-forming area has a mask bridge extending, transversely with respect to the channel etching slit, across the proximal slit end thereof.

In a further improvement in terms of a defined configuration of the holding part, it is proposed that the etching mask is provided with a sacrificial continuation, which is arranged at a proximal distance downstream of the channel etching slit and which serves to screen an etching agent effect in the mouth area of the collecting channel.

For the radial screening of a half space behind a mask edge, it is advantageous if the sacrificial continuation protruding freely on the mask edge is defined by an arc shape, in particular a circular arc shape, in an edge area directed away from the proximal slit end of the channel etching slit. The dimensions of the sacrificial continuation are to be adapted to the undercutting width of the etching agent, such that the sacrificial continuation is completely etched off to its proximal base. In principle, other geometries of the sacrificial continuation are also conceivable, for example rectangular or triangular, in order to make available a screening surface that has a suitable edge distance and a certain expanse for protecting the mouth area of the collecting channel from the etching medium.

In another embodiment, the etching mask is provided, on both sides of the substrate, with a tip-forming area in order to form a tip contour, wherein the channel-side tip-forming area is arranged distally in front of the tip-forming area lying on the opposite side. In this way, sufficient substrate material is also available in the area of the tip for a collecting channel that is routed as far forward as possible, while the cutting action is not impeded by interference contours on the opposite side.

In order to further reduce any interference contours, it is advantageous if the etching mask, on its opposite side directed away from the channel etching slit, has an auxiliary opening, in particular for avoiding undercut edges in the area of the tip.

Advantageously, the auxiliary opening is arranged in a tip-forming area of the etching mask at a lateral distance from a mask edge. In this connection, it is particularly expedient if the auxiliary opening has two auxiliary opening limbs extending toward each other in a V shape in the distal direction, and if the auxiliary opening has a distal auxiliary opening continuation, which extends in the distal direction beyond the auxiliary opening limbs and which is preferably designed as a slit or series of holes.

To avoid barbs or undesired humps, the end of the auxiliary opening continuation, seen in the proximal direction, should lie behind the distal end of the tip to be formed.

It is accordingly expedient if the auxiliary opening is Y-shaped, wherein the connection point of the opening limbs extending toward each other is arranged at a distal distance from the tip contour to be formed.

For samples to be already taken up in the skin, it is particularly advantageous if the channel etching slit is extended so far into a distal tip-forming area of the etching mask that the collecting channel terminates at a distance of 50 to 1000 μm, optionally 150 to 400 μm, before the distal end of the tip.

In another advantageous embodiment, the tapered end portion of the channel etching slit is reduced in width, along a length in the range of between 100 and 300 μm, by 0.4 to 0.6 times its initial width, toward a blunt end edge.

A further aspect of an embodiment of the invention concerns a piercing element with an elongate shaft, a distally protruding tip, a proximal holding part, and a laterally open collecting channel that collects bodily fluid and extends along the shaft as far as the area of the tip, wherein the collecting channel, at least at one end portion, extends with a continuously decreasing cross-sectional area and is formed by a mask-etching method as claimed.

The invention is explained in more detail below on the basis of an illustrative embodiment depicted schematically in the drawing, in which.

Figure 7:
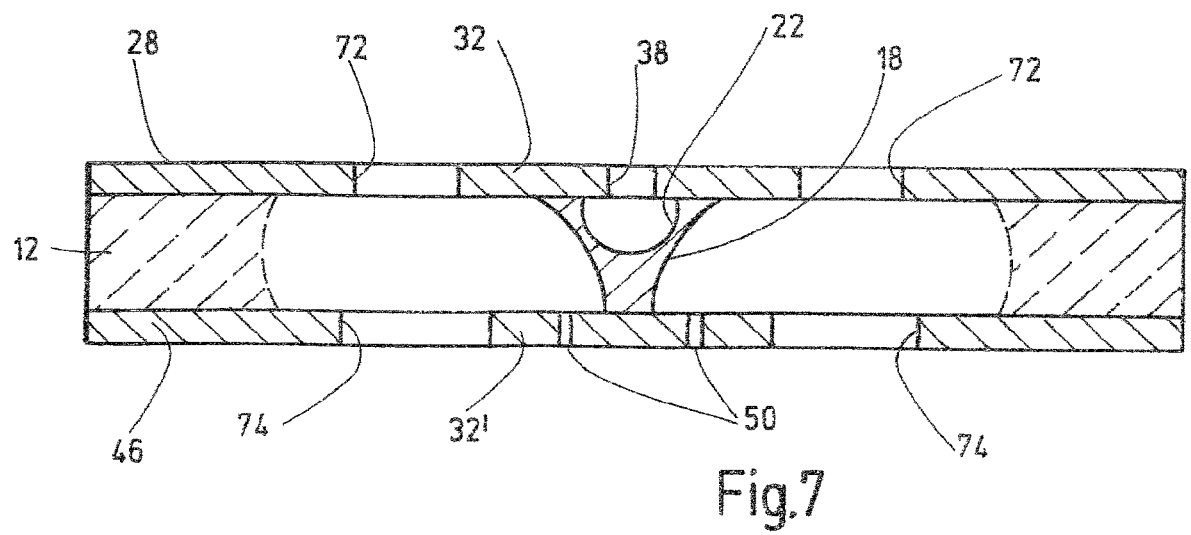
Figure 8:
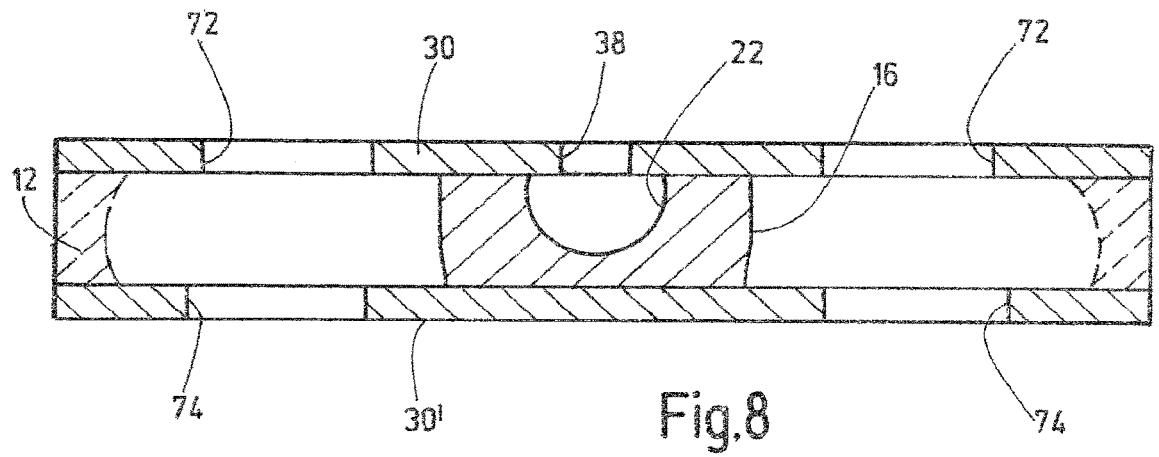
Figure 9:
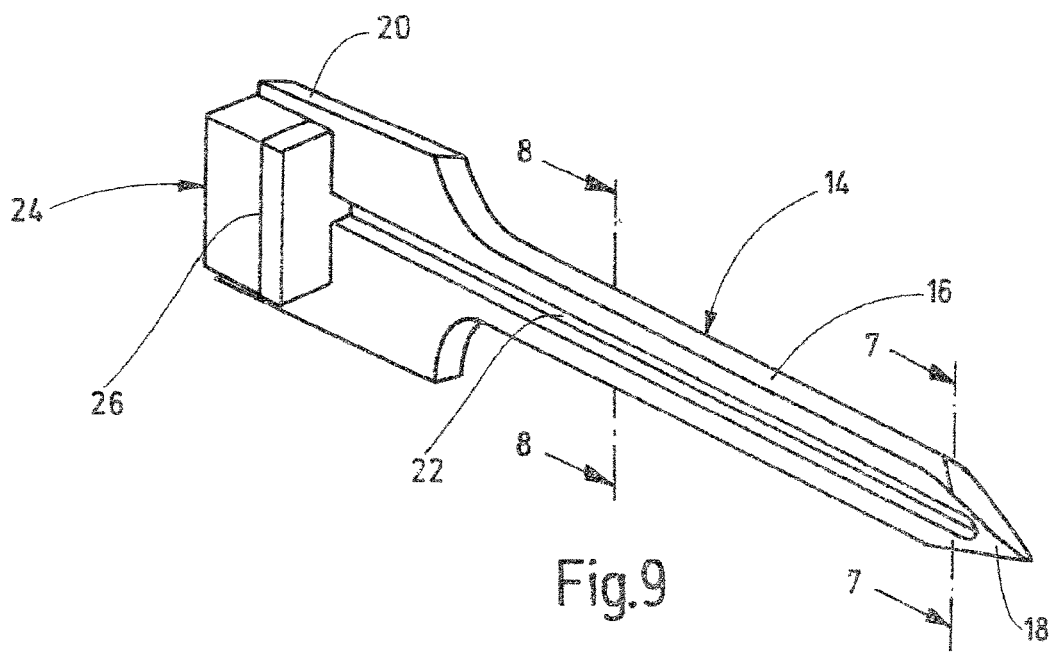

FIGS. 7 and 8 show a cross section through the etching mask and the piercing element along the section lines 7-7 and 8-8 in FIG. 9; and FIG. 9 shows a perspective view of the piercing element formed as a part made by chemical blanking, in conjunction with a test element flanged on at the proximal end.

An etching mask 10 shown in the drawing is applied as a double-sided layout onto the two sides of a thin stainless steel substrate in order to form a piercing element 14 as a part made by chemical blanking which, according to FIG. 9, has an elongate shaft 16, a distally protruding tip 18, a proximal holding part 20, and a collecting channel 22 that collects bodily fluid (blood, tissue fluid) from a skin incision and extends along the shaft 16 as far as the area of the tip 18 and is half-open or groove-shaped along its length. The piercing element 14 can be combined, as an integrated diagnostic consumable, with a test element 24, in order to transfer the sample fluid received in the capillary collecting channel 22 to a reagent layer 26 for determining an analyte (e.g. glucose). The test element 24 can be fixedly integrated on the piercing element 14 right from the outset, or it can be connected to the piercing element 14 only later for the transfer of the sample.

The etching mask 10 can be structured on the substrate 12 by photolithography, i.e. by exposure and washing out from photoresist, in a manner known per se. Through the recesses in the thus generated etching mask 36, the substrate 12 is then subjected to an etching agent, wherein the covered or masked areas are etched free according to the basic shape. It must be ensured that the material removal takes place not only depthwise but also by back-etching or undercutting of edge contours of the etching mask 10. As a result of external parameters influencing the substrate or as a result of material properties of the substrate, the etching process can also take place anisotropically, i.e. the lateral undercutting rate or width is then greater or lesser then the depth etching rate.

Figure 1:
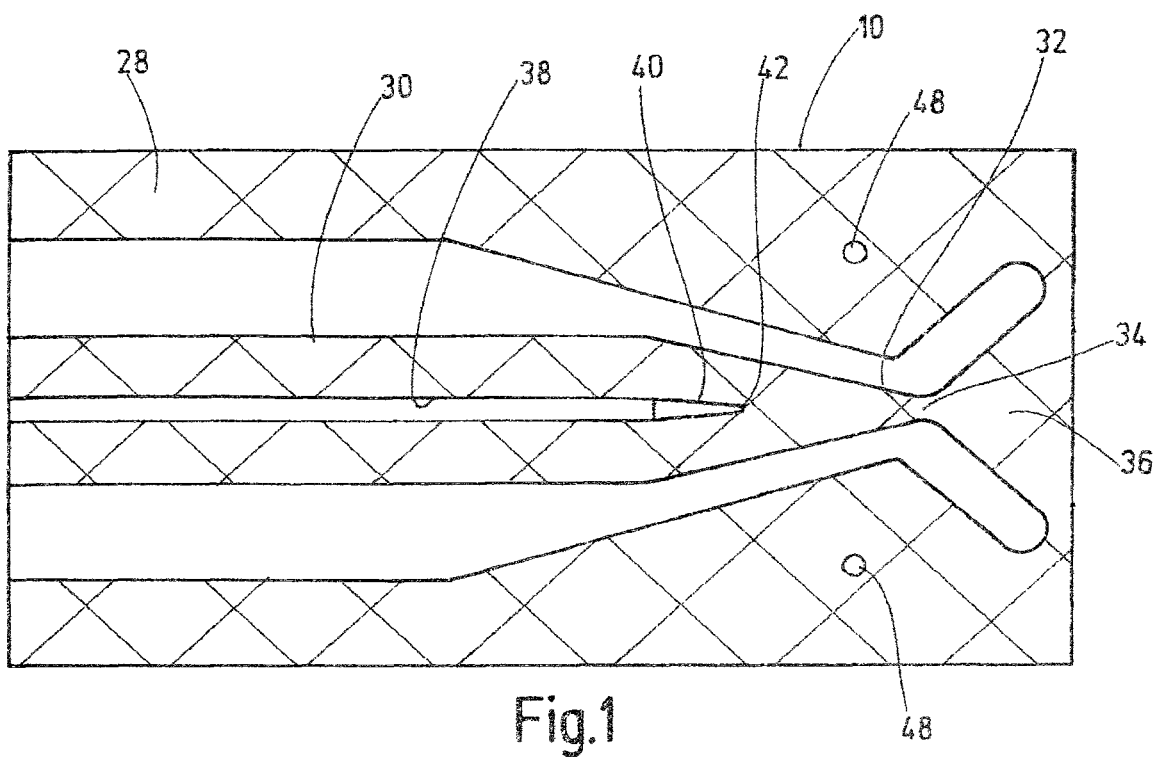
FIG. 1 shows a plan view of a distal, channel-side mask portion of an etching mask for producing a piercing element provided with a collecting channel.

The channel side 28 of the etching mask 10 in a distal portion shown in FIG. 1 has a shaft-forming area 30 for the shaft 16, and a tip-forming area 32 for formation of the tip 18. Starting from a constriction 34, the tip-forming area 32 is adjoined in the distal direction by a widening screening area 36, which prevents frontal etching-off of the tip 18, such that a particularly sharp tip contour is etched free only by lateral undercutting of the tip-forming area 32.

Further details of such screening for contouring of the tip are set out in WO 2006/066744, to which reference is made in this connection. In the latter, however, the distally protruding tip area is arranged on the substrate side (designated there as rear side) directed away from the capillary channel, whereas the capillary channel open at the front is laterally limited only behind the tip.

In the mask layout according to the invention, a channel etching slit 38 is provided on the channel side 28 for unilateral (groove-shaped) etching of a collecting channel 22, which terminates in the area of the tip 18 and is closed at the front. For this purpose, a distal end portion 40 of the channel etching slit 38 is designed to taper toward the distal slit end 42 lying in the tip-forming area 32.

Figure 2:
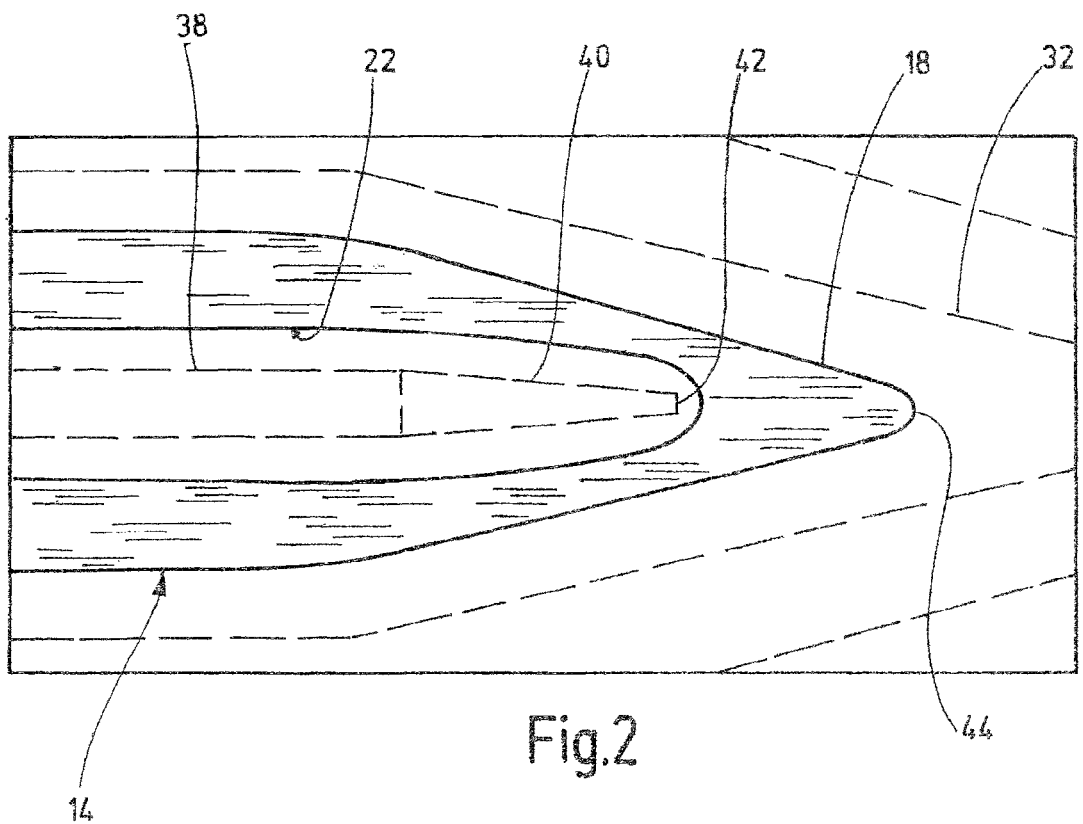
FIG. 2 shows an area of the piercing element generated with the mask portion according to FIG. 1.

FIG. 2 shows an enlarged detail of the etching mask 10 according to FIG. 1 in broken lines, in conjunction with the etched-free distal portion of the piercing element 14. It will be seen from this that the linear taper of the end portion 40 of the channel etching slit 38 is chosen such that the etched collecting channel 22 extends with continuously decreasing width and depth into the area of the tip 18.

The substrate thickness is expediently in the range of 100 to 300 μm. The width of the channel etching slit 38 in the central part can be about 100 to 150 μm, while the tapered end portion 40, along a length of 100 to 300 μm corresponding approximately to the substrate thickness, is reduced by approximately half its initial width toward a blunt end edge forming the slit end 42. It can thereby be achieved that the collecting channel 22 terminates at a short distance in the range of 150 to 400 μm before the distal end 44 of the tip 18.

Figure 3:
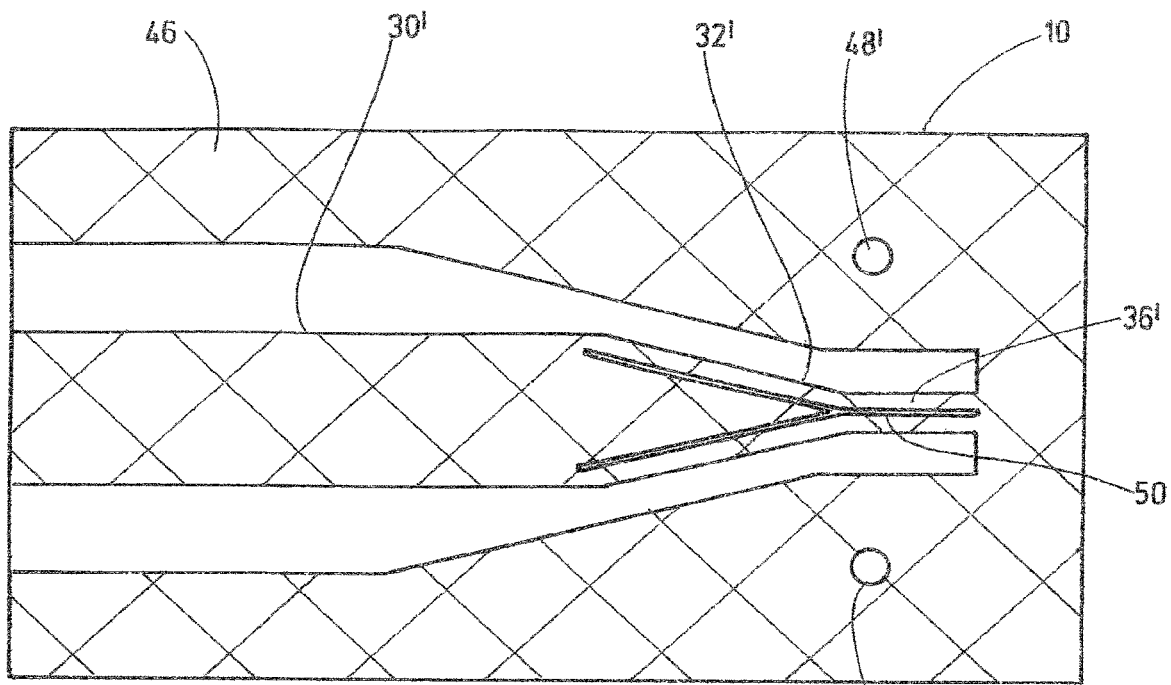
FIG. 3 shows a distal, rear-side mask portion in a view corresponding to FIG. 1.

FIG. 3 shows a distal portion of the etching mask 10 on the opposite side 46 directed away from the channel side 28. The two mask sides 28, 46 are positioned relative to each other such that the positioning or indexing holes 48, 48' lie concentrically with respect to one another. Also on the opposite side 46, the etching mask 10 has a shaft-forming area 30' for the shaft 16, and a tip-forming area 32' for the formation of a tip contour. A screening area 36' is arranged distally in front of the tip-forming area 32' in order to avoid bluntness at the front. In addition, a Y-shaped auxiliary opening 50 is provided for avoiding undercut edges and humps in the area of the tip contour on the channel opposite side 46, as is explained in more detail below.

The tip-forming area 32' on the opposite side 46 is set back in the proximal direction in relation to the channel-side tip-forming area 32, such that the tip 18, seen in the longitudinal direction, has a convex rounding starting from the distal end 44.

Figure 4:
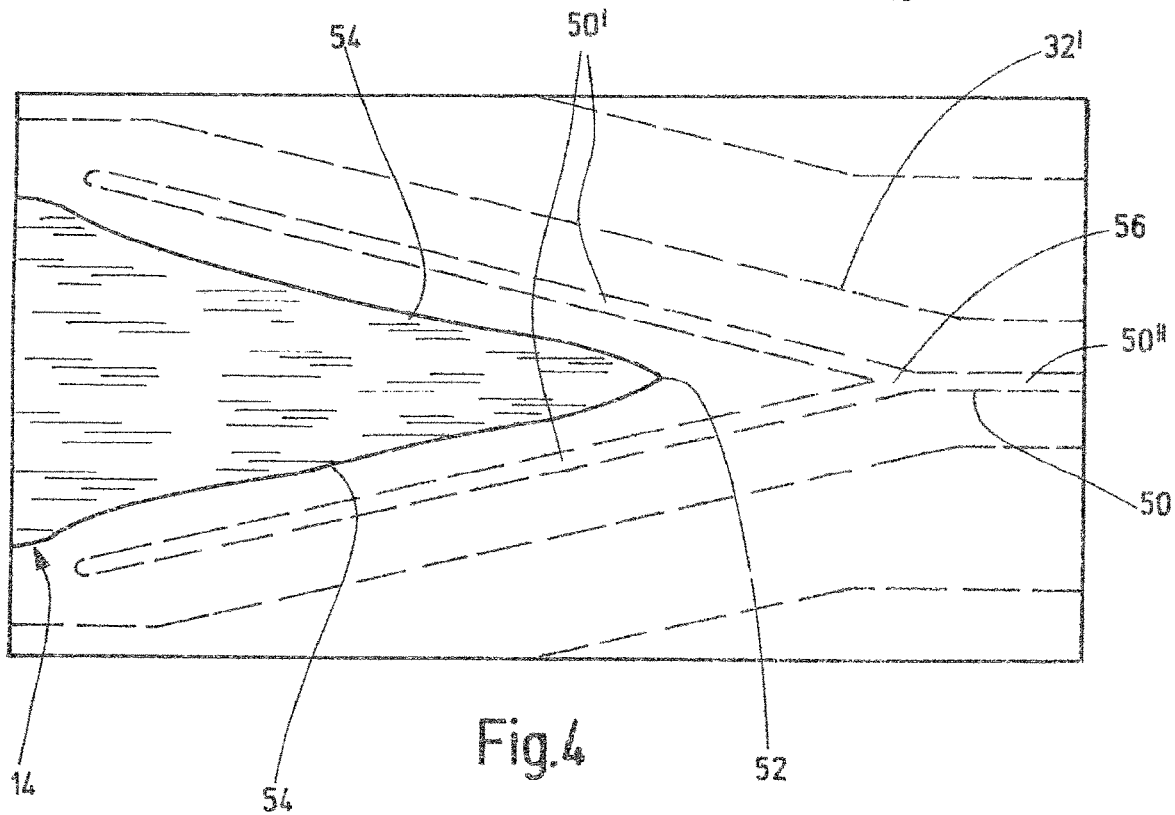
FIG. 4 shows an area of the piercing element generated with the mask portion according to FIG. 3.

As will be seen from FIG. 4, a tip contour tapering in a wedge shape via edges 54 to a vertex 52 is generated on the piercing element 14 by the tip-forming area 32' on the opposite side 46. The vertex 52 expediently lies, by more than the substrate thickness, in the proximal direction behind the channel-side distal end 44. The opening limbs of the auxiliary opening 50, which spread out approximately parallel to the edges 54, ensure that the edges 54 are rounded convexly in cross section by additionally penetrating etching agent and do not form a hollow. Correspondingly, the connection point 56 of the opening limbs 50' tapering toward each other is arranged distally in front of the vertex 52, such that no undercut barb impeding the incision forms in the longitudinal direction either. If the connection point 56 were arranged further forward, it would no longer be possible to achieve such an effect. By contrast, if it were moved further to the rear, a kind of transverse channel with a hump lying in front of it would be obtained. In order to avoid a contour of this kind that disrupts the needle incision, the auxiliary opening 50, starting from the connection point 56, has a distal base limb or auxiliary opening slit 50", which preferably extends with uniform width in the distal direction. The auxiliary opening slit 50" terminates at a proximal distance in relation to the channel-side distal end 44 of the tip 18 to be formed. In this way, the greater width of the channel-side tip-forming area 32 is taken into account.

Figure 5:
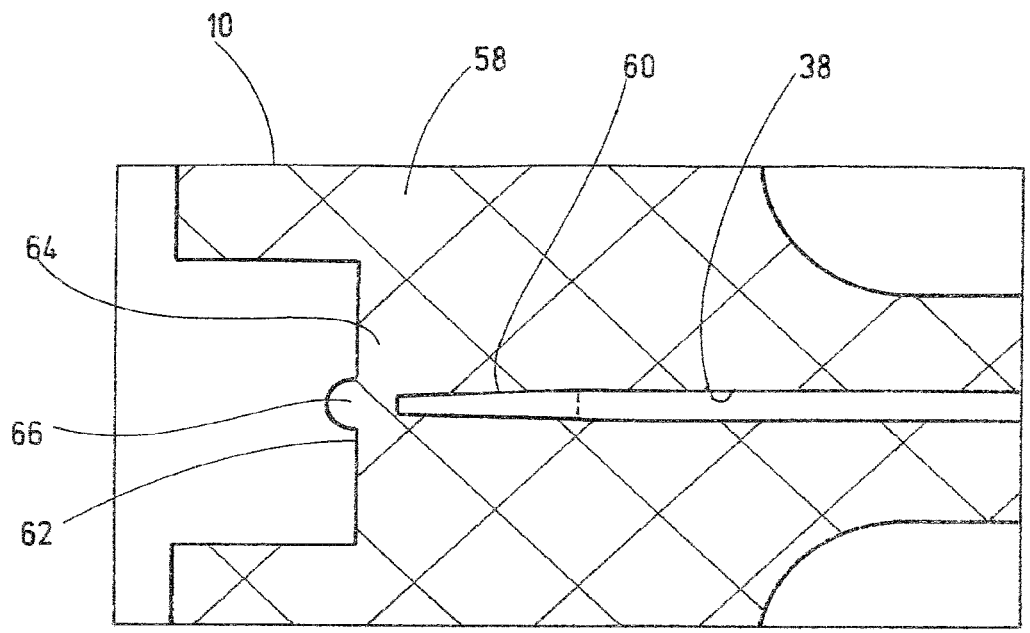
FIG. 5 shows a plan view of a proximal, channel-side mask portion.

FIG. 5 shows a proximal (rear) region 58 of the etching mask 10 on the channel side 28, which region 58 is provided for generating the holding part 20. The channel etching slit 38 can run out there in an end portion 60 tapering in the proximal direction. In principle, this rear end portion 60 can be dimensioned according to the front, distal end portion 40. The channel etching slit 38 can be positioned in the mask region 58 in such a way that the etched collecting channel 22 opens out at the front on the holding part 20, in order to permit a linear capillary transport of the sample fluid to the test element 24.

For docking of the test element 24, the mouth area of the collecting channel 22 should as far as possible have no widening of its cross section, as this could stop the capillary transport of liquid. Likewise, the test element 24 should lie flat thereon without an air gap. To achieve this, the etching mask 10 is provided with a flange-forming area 62, which adjoins the channel etching slit 38 in the proximal direction. The flange-forming area 62 has a mask bridge 64 which extends transversely with respect to the channel etching slit 38, across the proximal slit end thereof, which mask bridge 64, with uniform undercutting, leads in the distal direction to a rectilinear edge contour.

However, in addition to the distal undercut, the etching agent also flows via the channel etching slit 38 in the proximal direction and would lead to a corresponding widening of the etching at the mouth. In order to compensate for this effect, the etching mask 10 is provided with a sacrificial continuation 66, which is arranged downstream at a proximal distance from the channel etching slit 38 and which prevents a distal etching agent effect in the mouth area of the collecting channel 22.

To achieve this, the sacrificial continuation 66 protruding freely on the mask bridge 64 is arc-shaped in a proximal edge area, wherein the radius is adapted to the undercutting width such that the sacrificial continuation 66 is completely etched off.

Figure 6:
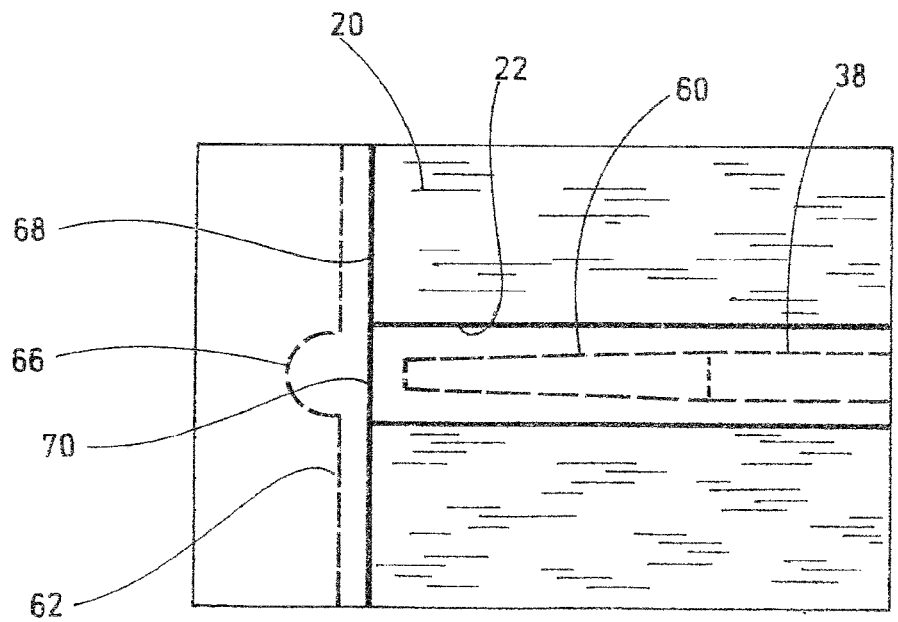
FIG. 6 shows an area of the piercing element generated with the mask portion according to FIG. 5.

FIG. 6 shows that, by means of the mask layout described above, a straight flange edge 68 is generated in the holding part 20 and leads to optimized sample transfer to the flanged-on test element 24. The sacrificial continuation 66 not only ensures a rectilinear boundary of the mouth 70 of the collecting channel 22, but also prevents an additional widening of the etching of the channel end portion. It will be appreciated that the proximal region of the etching mask 10 for the opposite side has no channel etching slit and, accordingly, has no sacrificial continuation. In other respects, however, it corresponds to the proximal region 58 on the channel side.

As is also clear from FIGS. 7 and 8, the structural contours and topography of the piercing element 14 are defined by the different mask layout on the two sides of the substrate 12. In addition to the surface etching of the fine collecting channel 22 on one side, the depth etching via the mask openings 70, 72 also achieves a separation of the chemical blanking part in the substrate, wherein a corresponding mask repetition permits the production of large batch numbers, if appropriate from roll to roll.

The invention claimed is:

1. A piercing element during a chemical blanking process, comprising:
   a substrate having opposing sides, wherein the substrate through the chemical blanking process is configured to form an elongate shaft, a distally protruding tip, a proximal holding part, and a laterally open collecting channel configured for collecting bodily fluid and extending along the elongate shaft as far as an area of the tip, wherein the collecting channel at least at one end portion extends with a continuously decreasing cross-sectional area; and
   a double-sided etching mask covering the opposing sides of the substrate, wherein a channel side of the double-sided etching mask is provided with a channel etching slit for unilateral etching of the collecting channel, wherein the channel etching slit has a proximal end portion and a distal end portion located opposite the proximal end portion, wherein the proximal and/or distal end portion of the channel etching slit tapers toward an end of the channel etching slit, wherein the double-sided etching mask, on an opposite side directed away from the channel etching slit, comprises an auxiliary opening having a Y-shape which serves to avoid making of undercut edges in the area of the distally protruding tip, wherein the distally protruding tip has a wedge shape defined by edges that meet at a vertex on the opposite side, wherein the auxiliary opening with the Y-shape has a connection point, at least a pair of opening limbs tapering towards one another at the connection point, and an auxiliary opening slit extending from the connection point.

2. The piercing element of claim 1, wherein the double-sided etching mask is provided with a flange-forming area, which adjoins the channel etching slit in a proximal direction, and the flange-forming area is undercut to form a flange edge forming a mouth of the collecting channel.

3. The piercing element of claim 2, wherein the flange edge is configured for flanging a test element onto the proximal holding part.

4. The piercing element of claim 3, wherein the flange-forming area comprises a mask bridge extending transversely with respect to the channel etching slit.

5. The piercing element of claim 1, wherein the proximal and/or distal end portion of the channel etching slit tapers linearly, such that the etched collecting channel extends in the direction of the taper with a constant or continuously decreasing cross-sectional area.

6. The piercing element of claim 1, wherein the channel etching slit in a proximal region of the double-sided etching mask is positioned such that the etched collecting channel opens out at a front end of the proximal holding part.

7. The piercing element of claim 1, wherein the double-sided etching mask comprises a sacrificial continuation, which is arranged at the proximal end portion downstream of the channel etching slit and which is used to screen an etching agent effect in a mouth area of the collecting channel.

8. The piercing element of claim 7, wherein the sacrificial continuation protrudes freely on a mask edge and is defined by an arc shape in an edge area.

9. The piercing element of claim 7, wherein dimensions of the sacrificial continuation are adapted to an undercutting width of the substrate in response to the etching agent, such that the sacrificial continuation is completely etched off to a proximal base for the sacrificial continuation.

10. The piercing element of claim 1, wherein the double-sided etching mask comprises, on both sides of the substrate, a tip-forming area in order to form a tip contour, wherein the tip-forming area on the channel side is arranged distally in front of the tip-forming area lying on a side opposite the channel side.

11. The piercing element of claim 1, wherein the double-sided etching mask, on the opposite side directed away from the channel etching slit, comprises the auxiliary opening which serves to avoid making of undercut edges in the area of the distally protruding tip.

12. The piercing element of claim 11, wherein the auxiliary opening is arranged in a tip-forming area of the double-sided etching mask at a lateral distance from a mask edge.

13. The piercing element of claim 11, wherein the auxiliary opening limbs extend toward each other in a V shape in a distal direction.

14. The piercing element of claim 11, wherein the auxiliary opening has a distal auxiliary opening continuation which extends in a distal direction.

15. The piercing element of claim 14, wherein a proximal end of the auxiliary opening continuation, as viewed in a proximal direction, is arranged behind a distal end of the distally protruding tip to be formed.

16. The piercing element of claim 14, wherein the auxiliary opening is designed as a slit or series of holes.

17. The piercing element of claim 11, wherein the connection point of the opening limbs is arranged distally from a tip contour to be formed on a side opposite the channel-side.

18. The piercing element of claim 1, wherein the channel etching slit is extended so far into a distal tip-forming area of the etching mask that the collecting channel terminates at a distance of 150 to 400 μm before a distal end of the distally protruding tip.

19. The piercing element of claim 1, wherein the proximal and/or distal tapered end portion of the channel etching slit is reduced in width, by 0.4 to 0.6 times an initial width of the channel etching slit, toward a blunt end edge.

20. The piercing element of claim 1, wherein the channel etching slit, at the proximal and/or distal end portion, is tapered toward the slit end along a length in a range of between 100 and 300 μm.

* * * * *